United States Patent [19]

Keene et al.

[11] Patent Number: 5,636,647

[45] Date of Patent: Jun. 10, 1997

[54] SOLUTION REMOVAL NOZZLE

[75] Inventors: Darren S. Keene; Russell J. Edwards, both of Jacksonville, Fla.

[73] Assignee: Johnson & Johnson Vision Products, Inc., Jacksonville, Fla.

[21] Appl. No.: 502,784

[22] Filed: Jul. 14, 1995

Related U.S. Application Data

[63] Continuation of Ser. No. 189,274, Jan. 31, 1994, abandoned, which is a continuation of Ser. No. 999,234, Mar. 29, 1993, abandoned.

[51] Int. Cl.$^6$ ........................................... B08B 3/02
[52] U.S. Cl. ............... 134/102.2; 134/186; 134/169 R; 134/901; 134/155; 134/177; 15/302
[58] Field of Search ........................ 134/155, 186, 134/102.2, 166 R, 169 R, 177, 201, 901, 182, 183, 175, 167 C, 166 C; 206/5.1; 15/302, 304, 322, 345; 34/224

[56] References Cited

U.S. PATENT DOCUMENTS

| | | | |
|---|---|---|---|
| 1,854,471 | 4/1932 | Hofmann | 15/304 |
| 2,538,366 | 1/1951 | Kerwin | 134/172 |
| 3,849,830 | 11/1974 | Wagner | 15/302 |
| 4,053,284 | 10/1977 | Posch | 15/304 |
| 4,341,568 | 7/1982 | Christensen | 15/304 |
| 4,635,665 | 1/1987 | Namba et al. | 134/167 R |
| 4,675,067 | 6/1987 | Valley | 134/186 X |
| 4,733,428 | 3/1988 | Malinge et al. | 15/302 |
| 4,986,290 | 1/1991 | Oguma et al. | 134/901 |
| 5,080,839 | 1/1992 | Kindt-Larsen | 264/2.6 |
| 5,094,609 | 3/1992 | Kindt-Larsen | 425/445 |
| 5,158,101 | 10/1992 | Sakka | 15/302 |
| 5,176,157 | 1/1993 | Yoshihara et al. | 134/186 |
| 5,195,549 | 3/1993 | Doams | 134/901 |

FOREIGN PATENT DOCUMENTS

| | | | |
|---|---|---|---|
| 64 381 | 11/1982 | European Pat. Off. | B29D 11/02 |
| 453 231 A2 | 10/1991 | European Pat. Off. | B29D 11/00 |
| 1942201 | 7/1970 | Germany | 15/302 |
| 61-97934 | 5/1986 | Japan | 15/345 |
| 1-31973 | 12/1989 | Japan | 134/901 |
| 2-254416 | 10/1990 | Japan | 134/901 |
| 1340826 | 9/1987 | U.S.S.R. | 15/304 |

*Primary Examiner*—Frankie L. Stinson

[57] ABSTRACT

An apparatus and a method for removing a liquid from a container having a bowl and a flange, the bowl holding the liquid and containing a hydrophilic ophthalmic lens, wherein there is provided a nozzle with a central face and a shoulder around the periphery of the face. The shoulder has a sealing means which is sized to fit on the flange of the container, where it forms a sealed volume above the container bowl, this volume including the volume of the bowl itself. The central face has through it at least one fluid entrance passage and at least one fluid exit passage arranged so that the flow is distributed substantially symmetric about the center axis of the lens so that when the purging fluid is introduced into the sealed volume, there is no migration of the lens. There is connected to the entrance passage a source of purging fluid that has a pressure and flow sufficient to remove substantially all the liquid through the exit passage.

9 Claims, 2 Drawing Sheets

SOLUTION REMOVAL NOZZLE

This is a continuation of application Ser. No. 08/189,274, filed Jan. 31, 1994, now abandoned, which is a continuation of Ser. No. 07/999,234, filed Mar. 29, 1993 now abandoned.

BACKGROUND OF THE INVENTION

This invention relates to a method and apparatus for removing processing liquid from a lens-bearing container during manufacture of molded ophthalmic lenses. This invention is suited to molded ophthalmic lenses such as hydrogel contact lenses, although the method is also suitable for other hydrophilic, high-precision ophthalmic lenses such as intraocular lenses. In particular, this method and apparatus are directed to the removal of deionized water from an ophthalmic lens package after lens inspection, and immediately prior to saline dosing and package sealing.

As the ophthalmic lens industry has grown, and in particular the industry related to supplying contact lenses that are provided for periodic frequent replacement, the number of lenses that need to be produced has increased dramatically. This has required manufacturers to strive for methods and apparatus that can be adapted to automated practices and perform with consistency.

Similarly, the promise of easier insertion of a folded or rolled intraocular lenses through a smaller incision has increased the interest in soft intraocular lenses for patients undergoing cataract removal and lens replacement.

Soft ophthalmic lenses for placement on the cornea or within the eye, such as contact lenses or soft intraocular lenses, can be made by a variety of techniques. Ophthalmic lenses can be made by spin casting a monomer material in a rotating mold then polymerizing the material so shaped. Another method used to manufacture both contact lenses and intraocular lenses is precision lathing of a piece of material which is then polished and used as a lens.

Recently the molding of soft contact lenses and soft intraocular lenses has come into favor. This technique has the advantages of repeatability and speed that compares favorably with the prior methods of manufacturing lenses, such as by forming a monomer or monomer mixture in a mold such as one made from polystyrene or polypropylene.

Techniques for successfully molding such lenses can be found in U.S. Pat. No. 4,495,313 and 4,640,489 to Larsen and U.S. Pat. Nos. 4,889,664; 4,680,336 and 5,039,459 to Larsen et.al. These patents specifically described the use of a diluent, a material which substitutes for water during the molding process, and which is replaced with water after the molding has been completed. The advantage of this technique is that the optical properties, size and shape of the lens thus made does not change as radically as with methods that do not utilize such diluent.

It is further known in the art to mold such ophthalmic lenses by forming a monomer or monomer mixture in a mold such as one made from polystyrene or polypropylene.

An example of this art can be found in U.S. Pat. No. 4,565,348 to Larsen. In contrast to the above polystyrene molds, another example is the use of polypropylene or polyethylene molds such as that described in U.S. Pat. No. 4,121,896 to Shepherd.

A practical method and apparatus for mass production of molded contact lenses using the above described processes is given in U.S. Pat. Nos. 5,094,609 and 5,080,839 both to Kindt-Larsen. Although the method and apparatus described therein are specifically directed to the removal of the diluent from the polymerized lens after molding and replacement with water, there is described in general the process steps that must be undertaken subsequent to the removal of the diluent and hydration of the lens.

In the 5,080,839 patent there is shown in FIG. 1 at element 130 a step described as deionized water removal. This removal is shown as taking place in an inspection carrier or final package. Subsequent steps are shown as saline deposition and sealing of the package.

The method and apparatus described in the above patents represents an improvement in the lens hydration process in that only deionized water is used for hydration, that is, release of the lens from the mold and hydrolysis of the diluent, instead of the performing the solution exchange operation with saline solution in a tank batch process. While this method has the benefits of no salt usage representing a cleaner and less corrosion prone system and accelerating processing times due to the deferment of meth-acrylic acid neutralization, it requires that the lens be transferred from the deionized water to a saline system so the lens can equilibrate to its final properties. Further because the inspection process is done in the primary package, it is necessary to exchange the deionized water with saline solution with the lens in the package and without removing the lens.

In the '839 patent it is stated that the deionized water is removed from the recesses of the inspection carrier and replaced with a saline solution which has a pH and osmolality compatible with the tears of the human eye. It is stated that alternately an aliquot of concentrated brine solution may be added to the deionized water such that the final solution has the same pH and osmolality mentioned above. Saline solution is used so that when the user removes the lens from the package, ready to insert the lens on the cornea of the eye, the pH and osmolality of the lens will be balanced with that of the eye and the lens will not irritate the eye when inserted. If the material from which the lens is made has an ionic characteristic, the salts in the saline solution will neutralize that ionic species. The neutralization can be done in the final package on the shelf outside the remainder of the manufacturing process. It may also be possible therefore to insert a small portion of solid sodium chloride salt into the ionized water to allow this stabilization to occur in the package after sealing.

Two considerations, however, make this approach impractical; first, the overall process requires a high degree of accuracy and repeatability. This is particularly difficult do to the small volume of the package cavity which is approximately 1 ml, and wherein any deviation in the amount of water present can represent a significant percentage in salinity. The direct addition then of either concentrated saline solution or solid sodium chloride salt would result in a significant variation and in final solution concentration.

The second problem with any attempt to partially remove the deionized water and replace it with concentrated saline is the handling of salt solution. As is well known, sodium chloride is corrosive to many materials and represents processing problems, such as salt crystal build-up after evaporation causing faulty seals, which is best avoided.

Great difficulties were encountered in achieving complete water removal by various methods. One such method was the insertion of a needle into the lens container to withdraw water. Experimentation with this method resulted in a repeatability for the six sigma range of 60 mg, which is approximately equal to a variability of 6% dilution of the final packing solution. Another method was the tilting of the package to an angle to allow the water to flow out of the package. In both instances, the amount of water remaining in the package afterward was variable and could not be relied upon to give the appropriate salinity with the addition of concentrated saline. A second problem with the tilting method is the presence of water on the remainder of the package interfering with final package sealing. Other methods to induce removal of the water in vapor form, such as microwave-induced evaporation, are too slow.

It is an object therefore, of the present invention to provide a method and apparatus that can quickly and completely remove the deionized water from the lens container.

It is a further object of the present invention to perform such removal without damaging or altering the final physical properties of the lens.

It is another object of the present invention to provide a method of establishing a final saline solution concentration that is highly accurate and repeatable so that the lens equilibrates to the proper oslmality.

It is a final object of the invention to provide a method and apparatus that achieves the above objects in such a controlled manner that the liquid is not distributed elsewhere so that moisture interferes with the subsequent sealing of the package.

SUMMARY OF THE INVENTION

The above objects are achieved and problems overcome with an apparatus and a method for removing a liquid from a container having a bowl and a flange, the bowl holding the liquid and containing a hydrophilic ophthalmic lens, wherein there is provided a nozzle with a central face and a shoulder around the periphery of the face. The shoulder has a sealing means which is sized to fit on the flange of the container, where it forms a sealed volume above the container bowl, this volume including the volume of the bowl itself. When sealed in this way, the central face is positioned above the lens within the bowl. The central face has through it at least one fluid entrance passage and at least one fluid exit passage. There is connected to the entrance passage a source of purging fluid that has a pressure and flow sufficient to remove substantially all the liquid through the exit passage. The entrance passage and exit passages are arranged so that the flow is distributed substantially symmetric about the center axis of the lens so that when the purging fluid is introduced into the sealed volume, there is no migration of the lens.

In the preferred embodiment, the entrance passage is located along the central cylindrical axis of the nozzle with a plurality of exit passages located in symmetric arrangement between the central axis and the shoulder. The preferred purging fluid is filtered air.

DESCRIPTION OF THE PREFERRED EMBODIMENT

Figure 1:
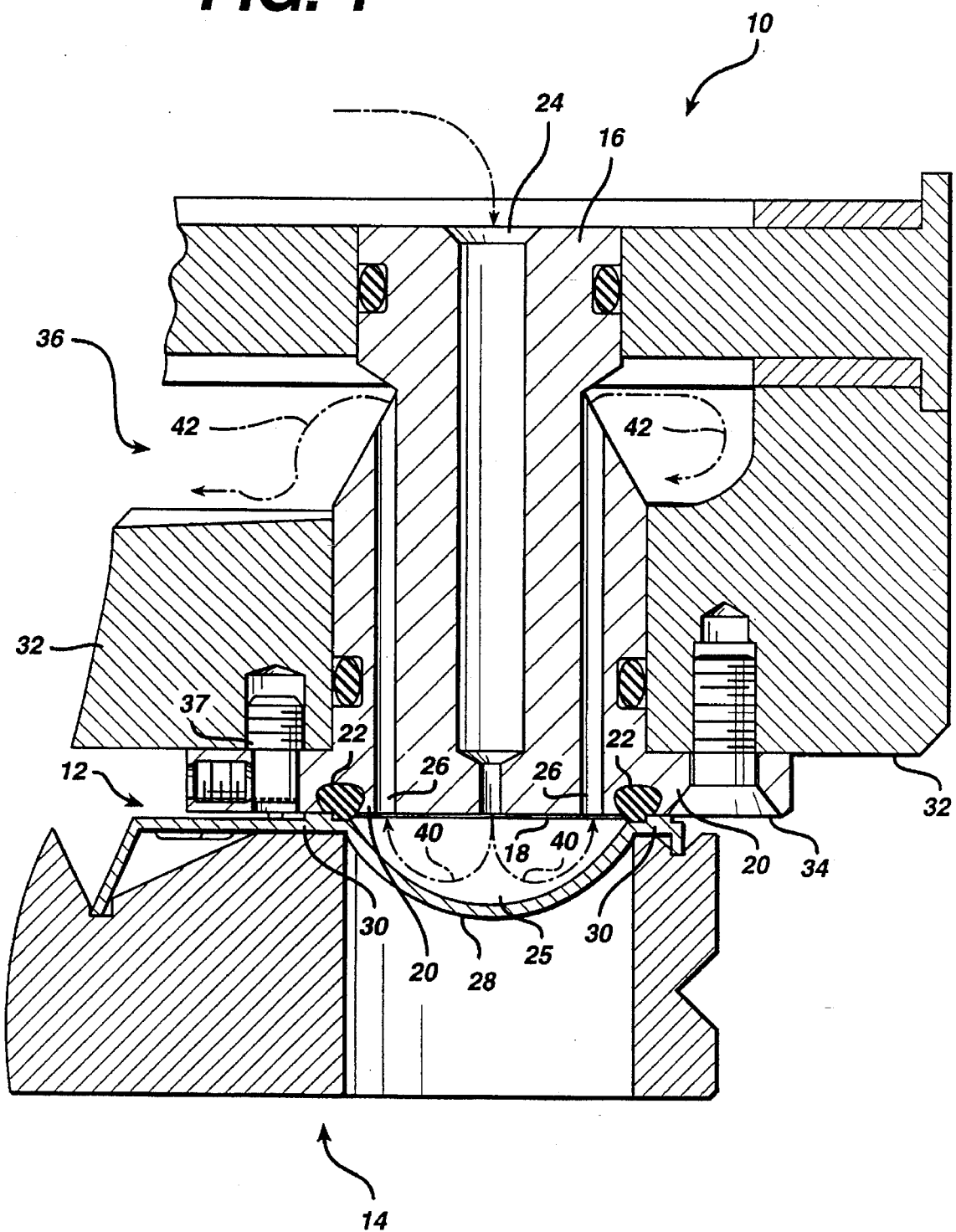
FIG. 1 is a cross sectional view of the apparatus of the present invention and shows as well the container which holds the liquid and ophthalmic lens.

Referring now to FIG. 1, there is shown the apparatus of the present invention 10 along with container 12 and container pallet 14. Solution exchange apparatus comprises solution exchange nozzle 16 having a central face 18 and shoulder 20. The nozzle also includes an entrance passage 24 and exit passages 26, while shoulder 20 has sealing means such as a silicon gasket 22.

While face 18 of the nozzle is shown as being flat, other shapes are acceptable, such as a tip in the center of the face which includes the entrance passage 24. Although this embodiment is acceptable and has certain advantages in retaining the lens in the container 12, it is not preferred because of positioning criticality and the possibility of snagging the lens.

Container 12 is generally comprised of a bowl portion 28 and a flange portion 30. A package design suitable for use with the apparatus of this invention and having properties compatible with obtaining the goals thereof is described in copending U.S. patent application Ser. No. 07/995,607 filed on Dec. 12, 1992 (attorney docket VTN-43) and entitled "Ophthalmic Lens Package".

Because it is desirable to process more than one container at a time, nozzle 16 is located within assembly 32, to which it is secured by attachment means such as screws 34. Multiple nozzles can be connected by a manifold to connect like entrance passages 24 or like exit passages 26 such as through a manifold 36. A manifold for the entrance passage 24 is not shown.

The entrance passage is connected to a source of purging fluid such as a gas (purified air) or saline solution.

In order to prevent the solution removal apparatus 10 from having the package 12 adhere to the apparatus after liquid removal, a bias means, such as spring plunger 37, is provided to supply a separation force between the two.

Figure 2:
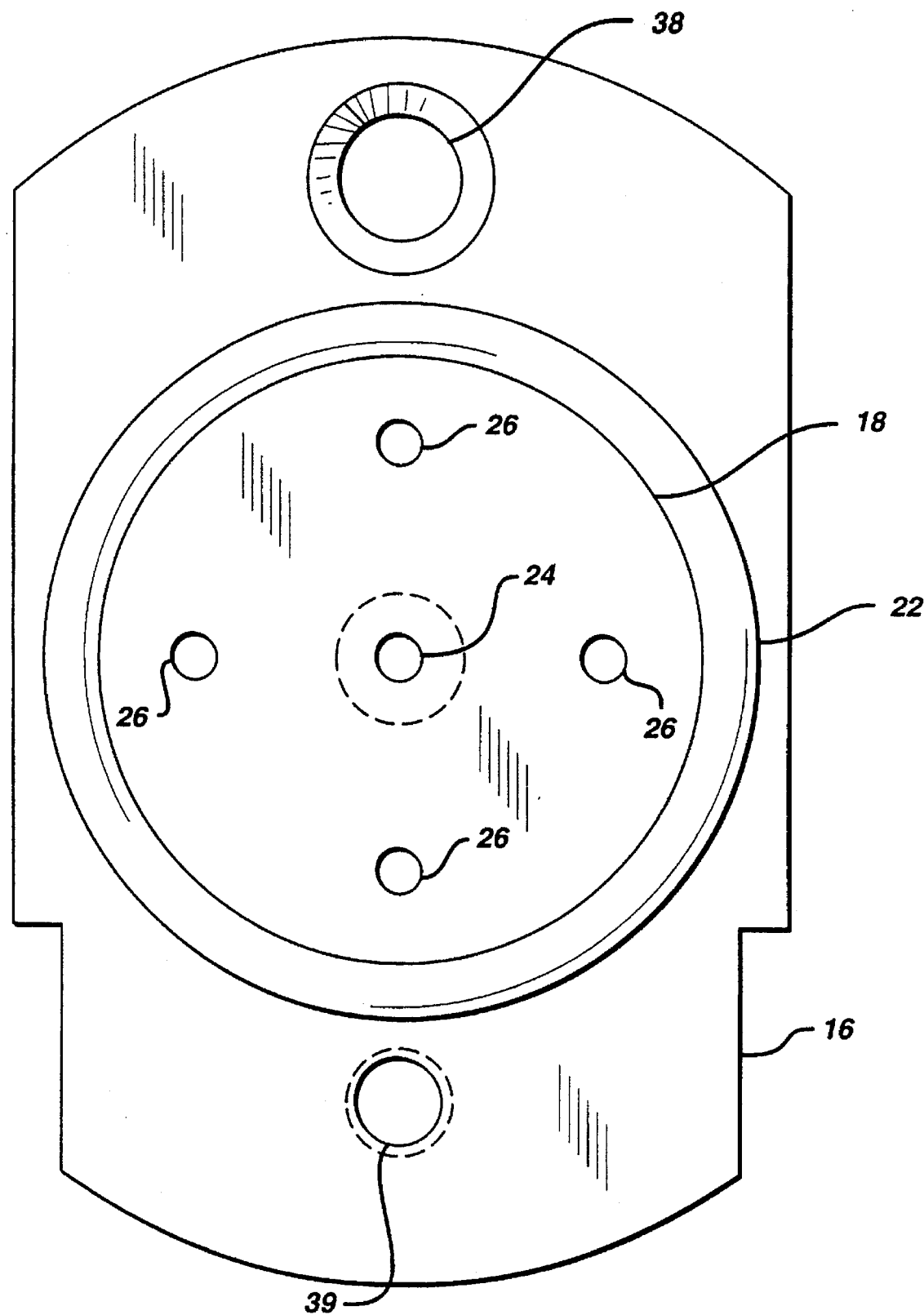
FIG. 2 is a bottom plan view showing the removal apparatus of FIG. 1.

Turning now to FIG. 2, nozzle 16 is depicted in a bottom plan view showing the surface of central face 18. Also shown is sealing means such as a silicon gasket 22 and the body of nozzle 16. The gasket 22 conforms to the shape of the package surface, but preferably the gasket contacts from its interior edge first, in order to prevent liquid from contacting the package sealing area of the flange. Holes 38 and 39 are shown indicating the location where attachment means 34 and spring plunger 37 are provided to attach the nozzle to the body of assembly 32, and provide separation force, respectively.

Directing attention to face 18, there is shown entrance passage 24 and four exit passages 26. As can now be more readily seen and appreciated, the entrance passage is located along the central axis of the nozzle 16 passing through the center of face 18. In addition, exit passages 26 are located symmetrically around entrance passage 24 between the center of face 18 and shoulder/sealing means 22. In this way, purging fluid provided through entrance passage 24 flows symmetrically through the sealed volume 25 and exiting through exit passages 26.

A specific embodiment achieving the objectives of this invention is defined by passages having a 0.062 inch diameter at the face. The entrance passage expands to 0.197 inches where it is connected to the purging fluid source. The diameter across the bowl and likewise the distance to the inner edges of sealing means 22, is 0.905 inches.

The central cylindrical axis of central passages 26 are located 0.310 inches from the center of the nozzle face 18. The purging fluid may be purified air or may be saline solution, which has the advantage of accomplishing deionized water removal and saline insertion in one step. The above described problems of handling a salt solution, however, are still present.

Two methods of providing the purging fluid at the proper pressure and flow rate are possible. The first is the application of the fluid, preferably sterile air or nitrogen, into the entrance passage at a relatively low pressure while sealing the nozzle by sealing means 22 against the flange 30 to create the sealed volume 25. This pressurizes the sealed volume and forces the deionized water out through the outlet holes as indicated by arrows 40. The liquid and purging fluid continue up passages 28 and exit through the manifold 36, as indicated by arrows 42.

The lens (not shown) is held on the bottom center of the cavity by the flow of purging fluid through the entrance passage 24. The effluent is routed away from the fixture by tubing connected to the manifold 36 to avoid contact with the package flange. Surprisingly, the lens/package system is extremely robust to this operation, and in fact, actually sticks to the package bowl by the surface tension of residual deionized water contained in the lens.

After this operation, the saline may be injected either through the same nozzle inlet port or in a separate operation using a metering pump, although it is preferred to provide the saline in a separate step to reduce the potential for salt related problems.

The second method of accomplishing the above may be to apply a vacuum to the manifold 36, rather than applying pressure to entrance passage 24. The vacuum source may be a Venturi type blower with a trap, or a pump. The sealed volume 25 may be sealed or vented using one or more of the exit passages 26 as vents.

In operation, lenses were processed using 30 psig pressure on the above described entrance passage for five seconds, then after the removal of the deionized water, dosed with 1 ml of saline solution. All 32 lenses were found to have been retained in the package and after dosing with the normal saline solution were allowed to equilibrate for approximately 12 hours for osmolality.

It was found that two seconds of injection of pressurized air at the above pressure and rate was found not to be long enough to move visible water residue. Ten seconds exposure to this process was found not to provide a measurable increase in the amount of water that could be removed.

These lenses were then inspected and found to have suffered no deleterious effects from the solution removal operation described above. In addition, prior to dosing with the saline solution, the amount of residual water was ascertained and found to be between 0.0110 and 0.0122 grams which corresponds to a 1.1 to 1.2 weight % dilution in 1.0 ml of saline.

As is readily apparent, variations in the above apparatus and method are possible without departing from the invention which is precisely delineated by the claims that follow.

I claim:

1. An apparatus for removal of a liquid from a container having a bowl portion and a flange portion, said bowl portion containing said liquid and containing an ophthalmic lens, said apparatus comprising:

a nozzle having a central face defined by a circumferential periphery and a shoulder about the circumferential periphery of said face, said central face having therethrough at least one fluid entrance passage and at least one fluid exit passage, said shoulder containing a sealing means, said shoulder sealing means combination sized to fit said sealing means on the flange portion of a container having a bowl portion and a flange portion, said bowl portion containing liquid with an ophthalmic lens therein and to position said central face above the lens within said bowl portion, a source of purging fluid connected to said entrance passage, wherein the purging fluid is introduced directly onto the lens and has a pressure and flow sufficient to remove substantially all of said fluid, said passages of said nozzle face located in an arrangement distributing the flow of said purging fluid and liquid in a substantially symmetric manner about the center axis of the lens.

2. The apparatus of claim 1 wherein said entrance passage is located along the central cylindrical axis of said nozzle and said exit passage exist in plurality between said entrance passage and said shoulder.

3. The apparatus of claim 1 wherein said nozzle further comprises a bias means for supplying a separation force between the apparatus and the container.

4. The apparatus of claim 1 wherein said purging fluid is a gas.

5. The apparatus of claim 1 wherein said purging fluid is saline solution.

6. An apparatus for removal of a liquid from a container having a bowl portion, said bowl portion containing said liquid and containing an ophthalmic lens, said apparatus comprising:

a nozzle having a central face defined by a circumferential periphery and a shoulder about the circumferential periphery of said face, said central face having therethrough at least one fluid entrance passage and at least one fluid exit passage;

said shoulder containing a sealing means, said shoulder sealing means combination sized to fit said sealing means on a container having a bowl portion and a flange portion, said bowl portion containing liquid with an ophthalmic lens therein and to position said central face above the lens within said bowl portion, a source of purging fluid connected to said entrance passage, wherein the purging fluid is introduced directly onto the lens and has a pressure and flow sufficient to remove substantially all of said fluid, said passages of said nozzle face located in an arrangement distributing the flow of said purging fluid and liquid in a manner so as to retain the lens in the bowl portion.

7. The apparatus of claim 6 wherein said nozzle further comprises a bias means for supplying a separation force between the apparatus and the container.

8. The apparatus of claim 6 wherein said purging fluid is a gas.

9. The apparatus of claim 6 wherein said purging fluid is saline solution.

* * * * *